US006046868A

United States Patent [19]

[11] Patent Number: 6,046,868

[45] Date of Patent: Apr. 4, 2000

Theriault et al.

[54] TRANSLATION SYSTEM FOR DIRECTING AN OPTICAL SIGNAL TO PREDETERMINED COORDINATES

[75] Inventors: Gregory A. Theriault, Encinitas; Leonard J. Martini; Leon V. Smith, both of San Diego, all of Calif.

[73] Assignee: The United States of America as represented by the Secretary of the Navy, Washington, D.C.

[21] Appl. No.: 09/015,431

[22] Filed: Jan. 29, 1998

Related U.S. Application Data

[63] Continuation-in-part of application No. 08/820,662, Mar. 17, 1997.

[51] Int. Cl.[7] .................... G02B 26/08

[52] U.S. Cl. .................... 359/896; 359/196; 359/198; 359/201; 359/202

[58] Field of Search .................... 359/196–226, 359/896, 831, 833

[56] References Cited

U.S. PATENT DOCUMENTS

| | | | |
|---|---|---|---|
| 5,289,307 | 2/1994 | Oldershaw et al. | 359/196 |
| 5,592,324 | 1/1997 | Inagaki et al. | 359/210 |
| 5,615,038 | 3/1997 | Suzuki et al. | 359/210 |

*Primary Examiner*—James Phan
*Attorney, Agent, or Firm*—Harvey Fendelman; Peter A. Lipovsky; Michael A. Kagan

[57] ABSTRACT

A translation system for directing an optical signal through predetermined coordinates of a window mounted in a soil penetration probe includes a tube having a sidewall and an aperture through said sidewall; an optically transparent window mounted in said aperture; an optical system for emitting an optical signal through said aperture; and a translation mechanism mounted within said tube. The translation mechanism may be selectively operated to translate independently and simultaneously the optical system along two orthogonal vectors so that the optical signal scans across the window. Scanning the optical signal extends the useful life of the window before its transmissibility becomes too impaired by damage caused from the optical signal.

12 Claims, 7 Drawing Sheets a
304
312
308
321
350
349
370
352
331
348
326b
328
326a
353
351
361
346
342
309
329
359
357
355
351b
351a
343
340
341
347a
347b
320
324
316
300

TRANSLATION SYSTEM FOR DIRECTING AN OPTICAL SIGNAL TO PREDETERMINED COORDINATES

CROSS-REFERENCE TO RELATED APPLICATIONS

This is a continuation-in-part of application Ser. No. 08/820,662 (Navy Case No. 78165) filed Mar. 17, 1997, pending, entitled Laser Induced Breakdown Spectroscopy Soil Contamination Probe.

BACKGROUND OF THE INVENTION

The present invention generally relates to the field of soil penetration probes, and more particularly, to a translation mechanism for directing an optical signal emitted by an optical system mounted in a soil penetration probe through predetermined coordinates of a window fitted in the wall of the probe.

Increasing concern with soil and groundwater contamination and governmentally mandated requirements to clean up hazardous waste sites have created a need for cost effective systems and methods for determining the characterization of a subsurface environments. In response to such needs, soil-penetrating probes have been developed generally comprising a tube with a tapered tip, which is forced into the ground. Instrumentation inside the tube detects various properties of the surrounding geological environment.

Laser induced Breakdown Spectroscopy (LIBS) is a method for detecting the presence of various elements in a sample by directing a high power emission from a laser onto the sample to form a plasma. The plasma then is analyzed spectroscopically to determine the composition of the sample. The LIBS technique offers promise as a method suitable for use with a soil-penetrating probe to detect heavy metal contamination in soil, because it is highly sensitive and requires no sample preparation. Usually the LIBS technique involves delivery of the laser energy to the sample through air due to the high power densities required to ionize the sample. Recently, fiber optic cable has been used successfully in LIBS measurements, allowing measurement of samples that are located at a considerable distance away from the excitation laser and analyzing equipment.

In a typical LIBS probe, laser light emitted from an optical fiber is collimated and then directed through a focusing lens and into the surrounding soil through a window mounted in the wall of the probe. However, the laser energy density required to stimulate the soil to generate atomic emissions tends to damage the sapphire window generally used in such probes. After several bursts of laser energy, the windows are damaged to the extent that the capability of the LIBS probe to detect atomic emissions from the soil is greatly impaired. Continued use of the probe requires that it be withdrawn from the soil so that the window may be replaced. Such repair is time consuming and hence, costly. Therefore, a need exists for a way to extend the life of the window to reduce the frequency of replacement.

SUMMARY OF THE INVENTION

The present invention provides a translation system for supporting an optical system so that an optical signal emitted from the optical system may be directed through predetermined coordinates. The invention is particularly well suited for directing the optical signal through predetermined coordinates of a window fitted in the wall of a soil penetration probe. Scanning the optical signal extends the useful life of the window by presenting fresh window area to the optical signal in applications in which the window becomes obscured due to damage from the optical signal. The translation system and optical system are typically mounted in a soil penetration probe. The invention includes a tube having a sidewall and an aperture through the sidewall; an optically transparent window mounted in the aperture; an optical system for emitting an optical signal through the aperture; and a translation mechanism mounted within the tube. The translation mechanism may be selectively operated to translate independently and simultaneously the optical system along two orthogonal vectors.

BRIEF DESCRIPTION OF THE DRAWINGS

Throughout the several views, like elements are referenced using like references.

DESCRIPTION OF THE PREFERRED EMBODIMENT

Figure 1:
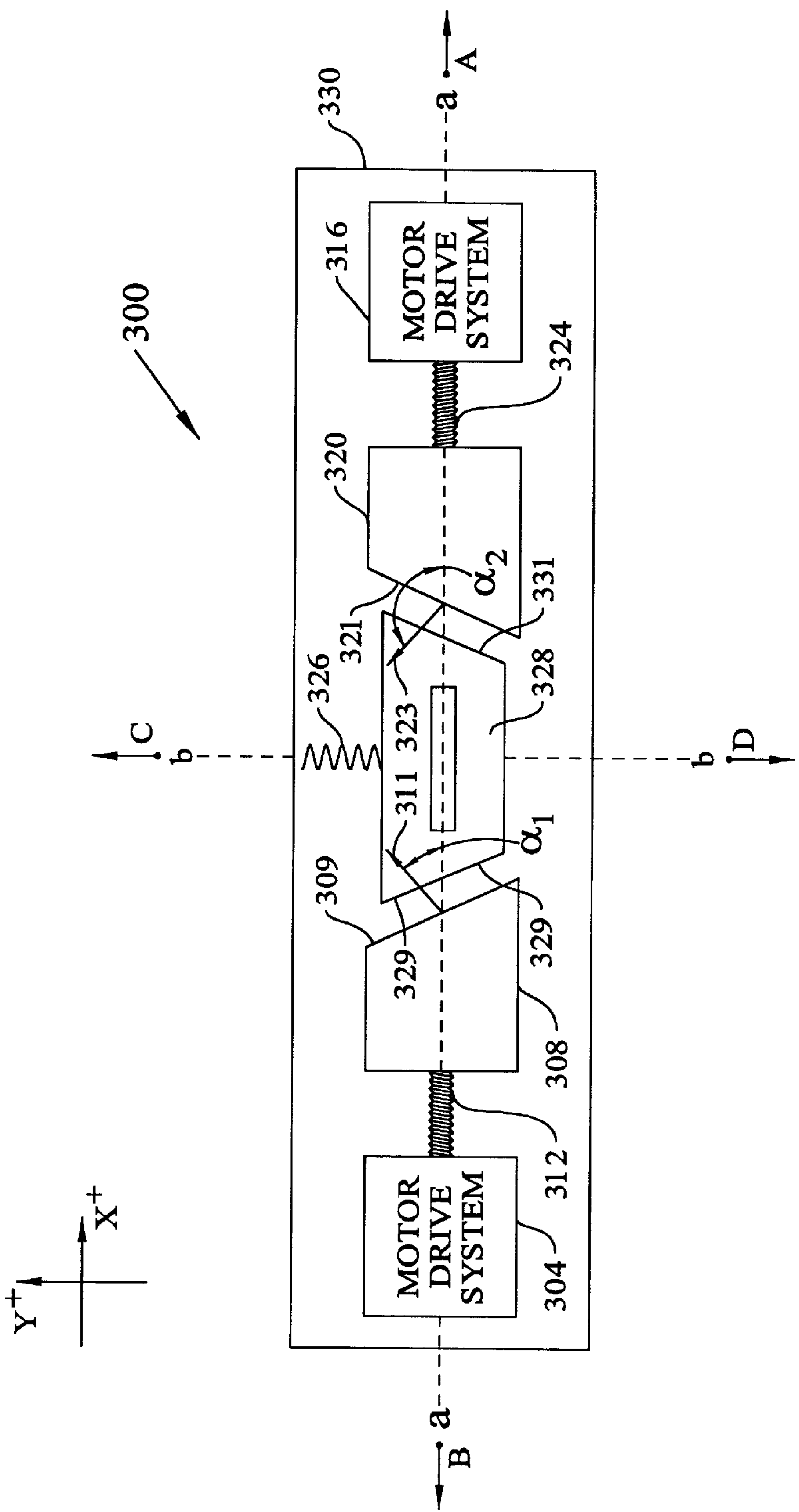
FIG. 1 is a block diagram of a translation system embodying various features of the present invention.

Referring to FIG. 1, there is shown a translation system 300 which supports an optical system 332 so that the optical output signal 382 (FIG. 5) of the optical system 332 may be scanned in two orthogonal directions independently of one another. The translation system 300 includes a motor drive system 304 which is coupled to a cam 308 by a screw drive 312, a motor drive system 316 coupled to a cam 320 by a screw drive 324, a cam follower 328, a frame 330, and a spring 326. Rotation of the screw drive 312 by motor drive system 304 causes cam 308 to slide within frame 330 along translation axis a—a. Similarly, rotation of the screw drive 324 by motor drive system 316 causes cam 320 to slide within frame 330 along translation axis a—a. Cam 308 has a generally planer cam surface 309 having a normal 311 which defines an angle $\alpha_1$ with respect to the translation axis a—a, where $\alpha_1 \neq 0$. Cam 320 has a generally planer cam surface 321 having a normal 323 which defines an angle $\alpha_2$ with respect to translation axis a—a, where $\alpha_2 \neq 0$, and preferably, where $\alpha_2 = 180° - \alpha_1$, and by way of example, $\alpha_1$ preferably may be in the range of about 30°. Cam follower 328 has cam follower surfaces, 329 and 331, which are parallel to cam follower surfaces 309 and 321, respectively. Spring 326 interposed between frame 330 and cam follower 328 forces cam follower 328 against cams 308 and 320.

When cams 308 and 320 are both directed to move in the direction of $\vec{A}$ by an equal distance, cam follower 328 and optical system 332 are moved in the +X direction. Conversely, when cams 308 and 320 are both directed to move in the direction of $\vec{B}$ by an equal distance, cam follower 328, and hence, optical system 332 are moved in the −X direction. When cams 308 and 320 are moved towards each other, the cam surfaces 309 and 321 pushing against cam follower surfaces 329 and 331, respectively, force cam follower 328 to move in the +Y direction of $\vec{C}$. When cams 308 and 320 are moved away from each other, the cam surfaces 309 and 321 spread apart so that spring 326 pushes cam follower 328 in the −Y direction of $\vec{D}$. The directions of $\vec{A}$ and $\vec{B}$ are both orthogonal to the directions of $\vec{C}$ and $\vec{D}$.

Figure 2:
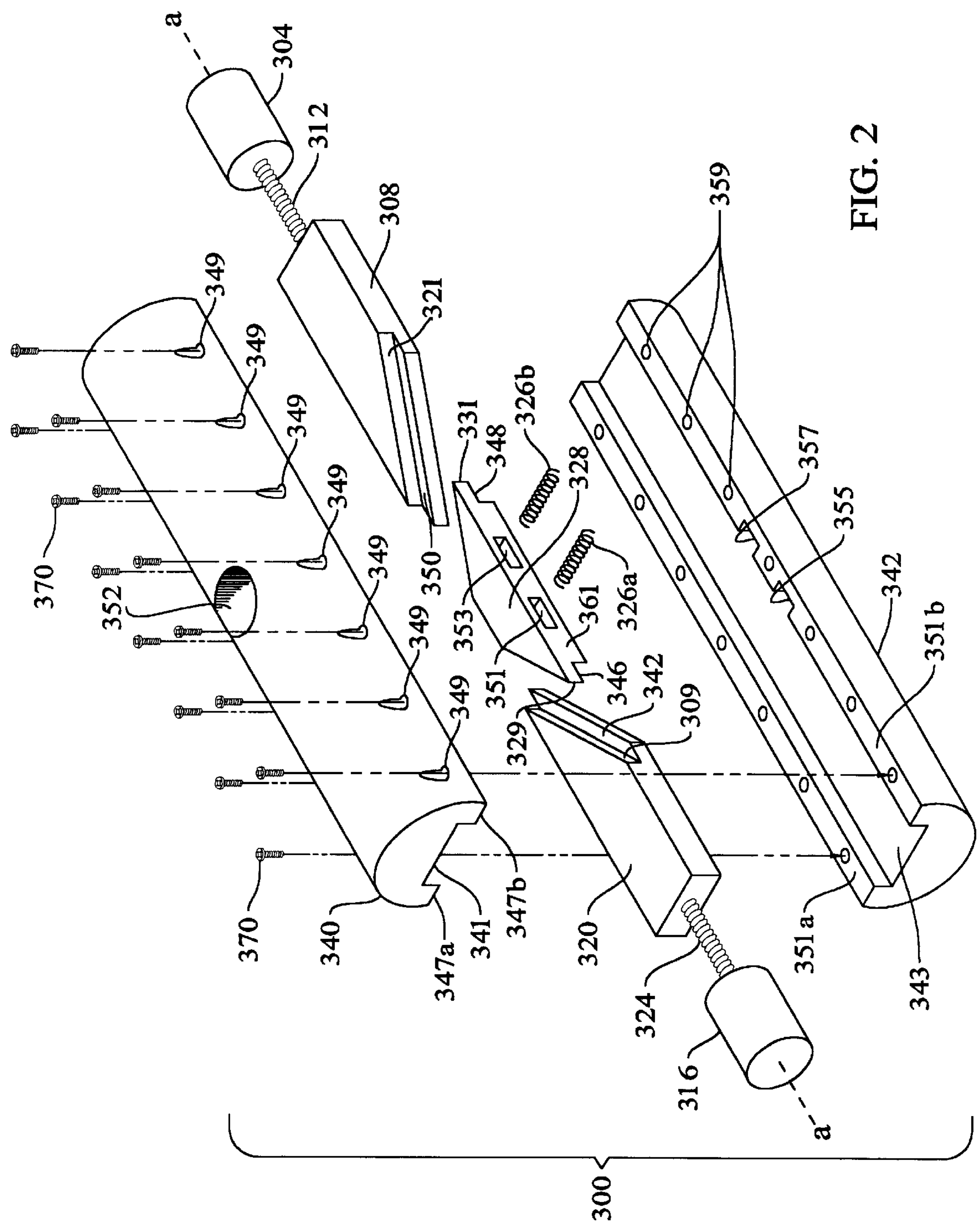
FIG. 2 is an exploded view of an example of one embodiment of the translation system of FIG. 1.
Figure 3:
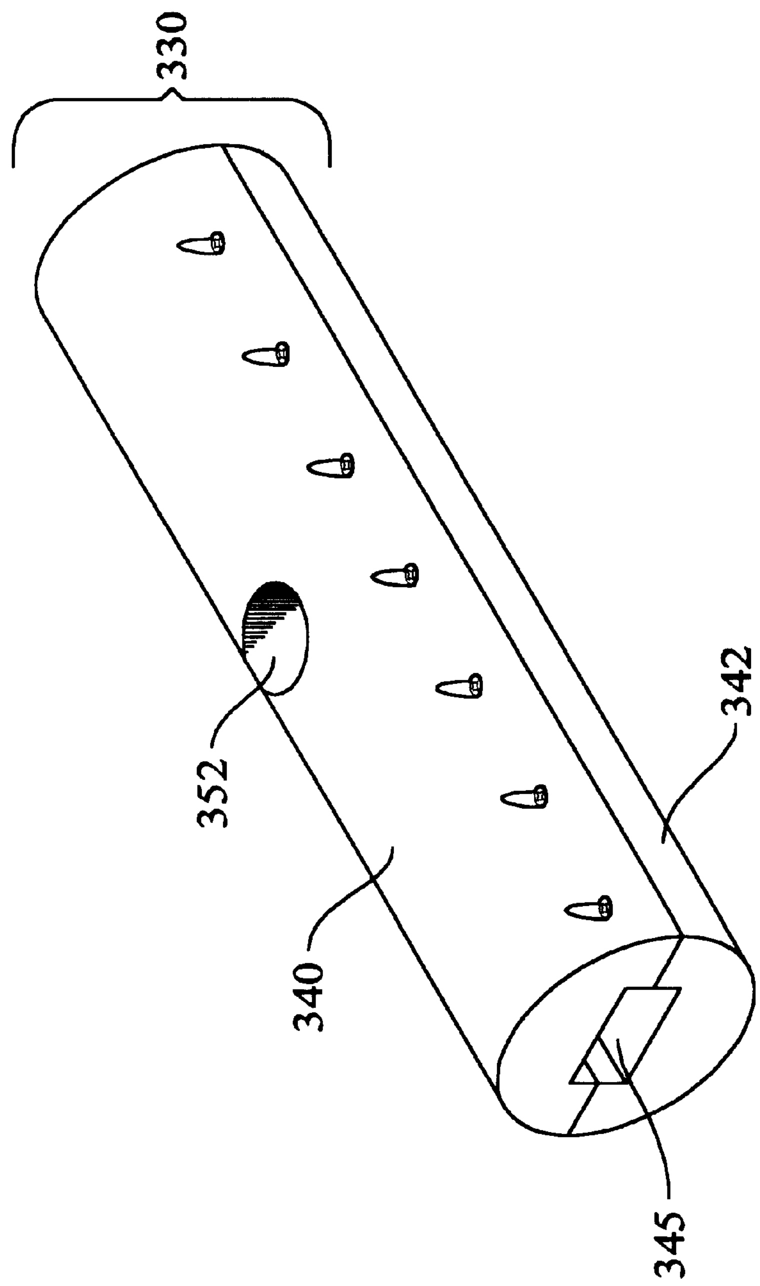
FIG. 3 is a cross-sectional view of the frame of FIG. 2.

An example of one embodiment of translation system 300 is shown in FIG. 2. Frame 330 preferably comprises cylindrical half-shells 340 and 342 in which are formed rectangular channels 341 and 343, respectively. When half-shells 340 and 342 are assembled, the rectangular channels 341 and 343 define a bore 345 having a rectangular cross-sectional area, as shown in FIG. 3, and the exterior of frame 330 is generally cylindrically shaped. Half shell 340 includes mounting surfaces 347*a* and 347*b* through which are formed apertures 349. Half-shell 342 includes mounting surfaces 351*a* and 351*b* in which are formed threaded apertures 359. The half shells 340 and 342 are assembled to form frame 330 whereby mating surfaces 347*a* and 351*a* are placed in contact with each other, and mating surfaces 347*b* and 351*b* are placed in contact with each other. The half-shells are fastened together by fitting threaded fasteners 370 through apertures 349 and threading them into threaded apertures 359. Aperture 352 is formed in cylindrical half-shell 340 and provides a portal through which optical signal (FIG. 5) may pass.

Still referring to FIG. 2, cam 320 may be generally shaped as a trapezoid having a generally planar cam surface 309 on which a lip, or flange 342 is formed at one end. Cam 308 is configured as generally a mirror image of cam 320. Cam 308 has a generally planar cam surface 321 on which a lip, or flange 350 is formed at one end. Cam follower 328 further includes lips, or flanges 346 and 348 formed at the undersides of planar surfaces 329 and 331, respectively. Cam follower 328 includes two slotted recesses 351 and 353 formed in sidewall 361, which receive springs 326*a* and 326*b*, respectively. Springs 326*a* and 326*b* are also fitted in slots 355 and 357, respectively, in flange 351*b* of half-shell 342 and are held in place when the shells are fastened together. Springs 326*a* and 326*b* urge cam follower 328 against cams 320 and 308. Screw drives 324 and 312 are threaded into cams 320 and 308, respectively, in accordance with well-known techniques. Screw drives 324 and 312 are coupled to the output shafts, not shown, of motor drive systems 316 and 304.

Figure 4:
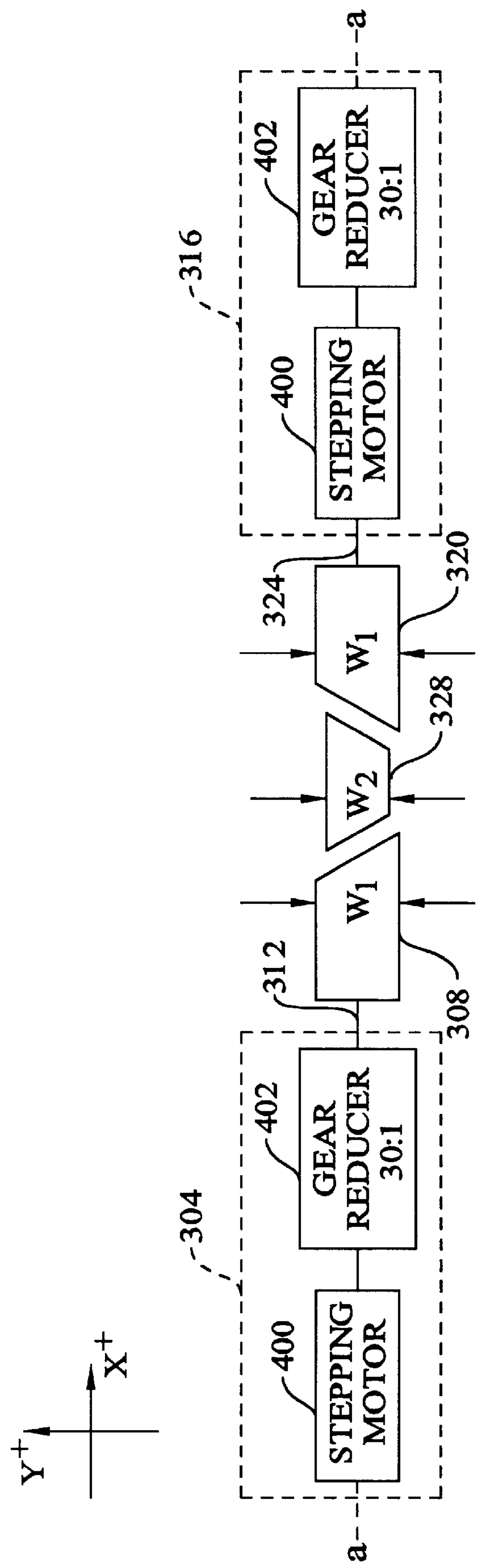
FIG. 4 shows an embodiment of the translation system wherein the motor drive systems each include a stepper motor and a gear reducer.

Cams 308 and 320 and cam follower 328 are preferably made of a material having self-lubricating properties, such as Nylon® or Delrin®, although in one embodiment of the invention, cam follower 328 was made of aluminum. Cams 308 and 320 are constrained to smoothly slide within bore 345 (FIG. 3) such that the lips 346 and 348 of cam follower 328 are in contact with lip 342 of cam 320 and with lip 350 of cam 308, respectively, in the manner of a lap joint. In the preferred embodiment of translation system 300, the angles $\alpha_1$ and $\alpha_2$ are on the order of about 30° and 150°, respectively, with respect to axis a—a. Moreover, as shown in FIG. 4, motor drive systems 304 and 316 may each be implemented to include a stepping motor 400 that is coupled to gear reducer 402 having, for example, a 30:1 reduction ratio. Screw drives 312 and 324 may each have 32 threads per inch, although other pitches may also be used. Cams 308 and 320 each have a width, $W_1$, transverse to axis a—a. Cam follower 328 has a width, $W_2$, transverse to axis a—a, where preferably, $W_2<W_1$ so that cam follower 328 has room to translate between cams 308 and 320 in the ±Y-directions within bore 345 of frame 330.

Figure 5:
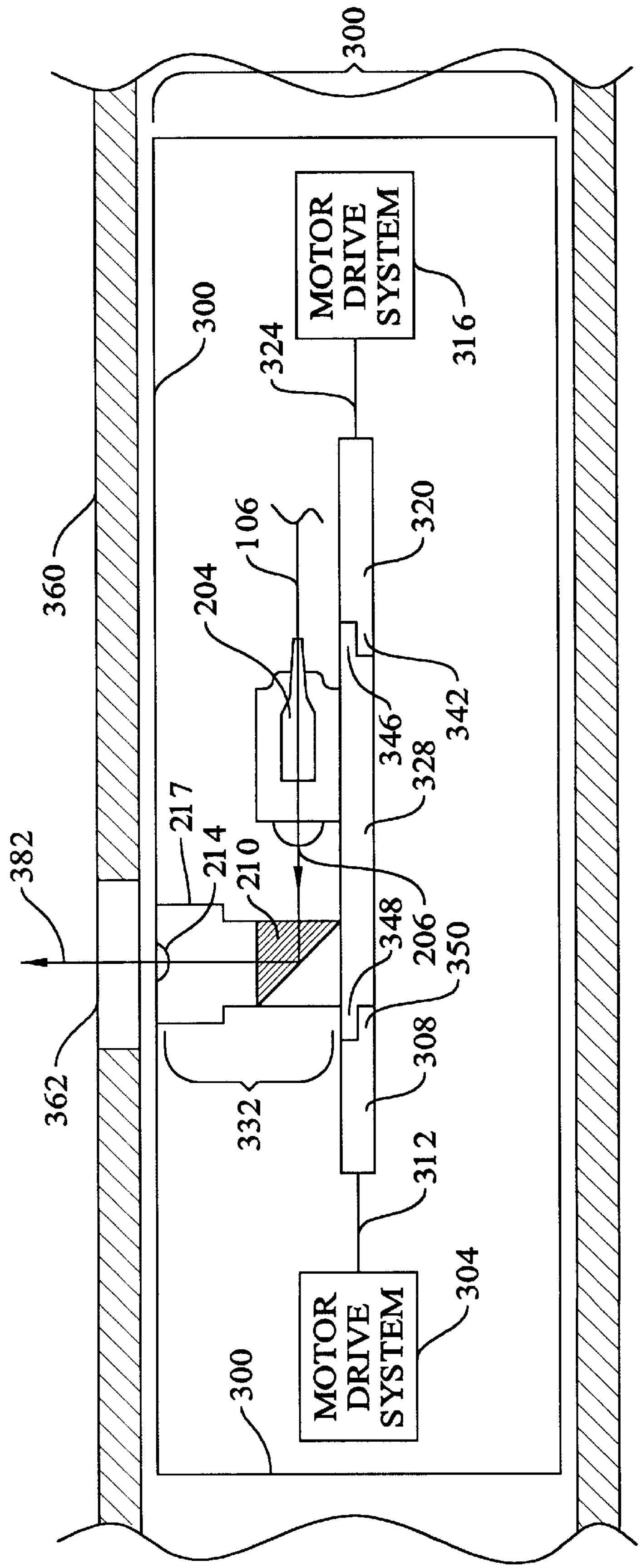
FIG. 5 shows an optical system mounted on the cam follower of the translation system all mounted within a tube.

Optical system 332 is described with reference to FIG. 5 and includes optical fiber 106, terminator 204, collimating lens 206, prism 210, focusing lens 214, and support structure 217 mounted to cam follower 328. Optical signal 382 is ejected from optical fiber 106, collimated by collimating lens 206 and then is reflected by about 90° by prism 210. The reflected optical signal 382 is focused by focusing lens 214 and is directed through sapphire window 362 of tube 360. Focusing lens 214 is affixed to support structure 217. Translation system 300 is typically mounted in tube 360, an element of a soil penetration probe. Optical fiber 106, terminator 204, collimating lens 206, prism 210, focusing lens 214, tube 360, and window 362 are functionally interrelated and characterized as described in application Ser. No. 08/820,662 (Navy Case No. 78165), filed Mar. 17, 1997, entitled Laser Induced Breakdown Spectroscopy Soil Contamination Probe, incorporated herein by reference. The optical system 332 may be mounted on cam follower 328 within frame 330 so that optical signal 382 may be directed through aperture 352 of frame 330 and window 362 fitted in tube 360 (FIG. 5).

Figure 6:
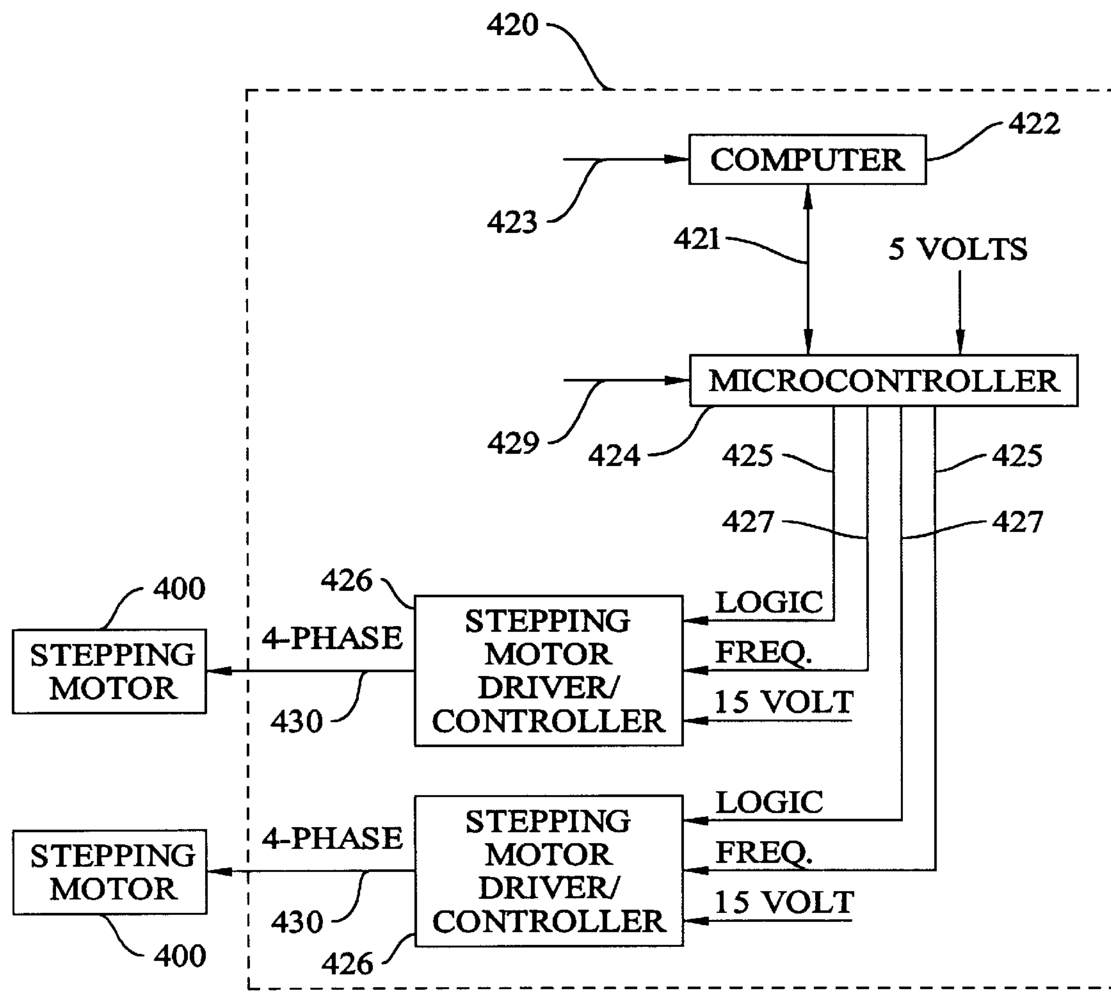
FIG. 6 is block diagram of the control system for controlling the operation of the stepping motors shown in FIG. 4.

FIG. 6 illustrates an example of control system 420 for directing the operation of motor drive systems 304 and 316, and includes a computer 422, microcontroller 424, and stepping motor driver/controllers 426. Computer 422, such as a Pentium®-based PC, receives an input command signal 423, which may include information such as operating system parameters, start-up, and shutdown commands. A host BASIC editor/terminal program resides in computer 422 and operates while cam follower 328 is translated, causing optical signal 382 to irradiate window 362 at predetermined locations. Signal 423 may be provided by an input device (not shown) such as a keyboard, or even another computer. Computer 422 provides command signals 421 to microcontroller 424, which implements a program that controls the directions and angular displacements of the stepping motors 400. Command signals 421, by way of example, is an RS422 formal differential serial data signal which includes the programming for microcontroller 424, where such programming is exemplified in APPENDIX 1. By way of example, microcontroller 424 may include an EEPROM programmed with a computer program, such as exemplified in APPENDIX 1, which controls the translation of cam follower 328 so that the optical signal 382 scans window 362 in a predetermined pattern. The program may be written in BASIC 3.0. Microcontroller 424 generates a signal pair comprising a logic signal 425 and frequency signal 427 for each particular stepping motor 400. Each signal pair comprising logic signal 425 and frequency signal 427 is provided to a stepping motor driver/controller 426. Each stepping motor driver/controller 426, in turn, generates an appropriately 4-phased motor control output signal 430 for controlling the direction of rotation and number of steps of a stepping motor 400. Representative implementations of microcontroller 424, stepping motor driver controllers 426, and stepping motors 400 are provided in TABLE 1. An important feature of microcontroller 424 is that the angular positions of the stepping motors 400 only change when the logic level of input signal 429 is at a first predetermined logic level, as for example, a logic "high," representing that optical signal 382 is being emitted from optical fiber 106.

Conversely, the motor drive systems 304 and 316 are inhibited when the logic level of signal 429 is at a second logic level, such as a logic low," representing that optical signal 382 is not being emitted from optical system 332. This feature provides the benefit of optimizing the available transparent area of sapphire window 362.

TABLE 1

| Element | Reference No. | Manufacturer | Model No. |
|---|---|---|---|
| Microcontroller | 424 | MICROMINT INC. | DOMINO-52A |
| Stepping motor driver/controller | 426 | HURST | 9550 |
| Stepping motor | 400 | HURST | BAS-12 |

Translation mechanism 300 has the ability to selectively move the optical system 332 mounted on cam follower 328 independently in two orthogonal (X and Y) directions, and for example, may be employed to move the optical system 332 in a circular or any other suitable pattern. The purpose of this translation is to scan optical signal 382 through different regions of optical window 362 to extend the operational life of the sapphire window. Such scanning presents fresh window area to the optical signal 382, since the energy from the optical signal impairs the transmissibility of the window if the optical signal 382 were to dwell too long on one region of the window.

Motion in the X-direction is described with reference to FIGS. 1 and 4. The rotational direction of stepping motor 400 of motor drive system 304 is considered counter-clockwise (CCW) when looking at stepping motor 400 in the −X direction along axis a—a. The rotational direction of stepping motor 400 of motor drive system 316 is considered counter-clockwise (CCW) when looking at stepping motor 400 in the +X direction along axis a—a. Each stepping motor 400 of motor drive systems 308 and 316 requires, by way of example, 20 steps for 1 rotation of its output shaft (not shown). As previously stated, gear reducers 402 have, by way of example, reduction ratios of 30:1. Therefore, 30 rotations of a motors 400 will result in 1 rotation of corresponding drive screw 312 or 324, where it is to be understood that stepping motors 400, and hence, drive screws 312 and 324 may be driven independently of one another. Converting the number of motor steps into a translation distance in inches is obtained by $$\frac{20\text{ Motor Steps}}{1\text{ Motor Rotation}} \times \frac{30\text{ Motor Rotations}}{1\text{ Drivescrew Rotation}} \times \frac{32\text{ Drivescrew Rotations}}{1''} = \frac{19200\text{ Steps}}{1''} \tag{1}$$

Therefore, 1" of motion of a cam 320 or 308 in the positive or negative X-direction along axis a—a requires 19200 steps of a motor 400.

Motion in the Y-Direction, i.e., perpendicular to axis a—a is described with reference to FIG. 1. Cam follower surfaces 329 and 331 define, by way of example, 30° and 150° angles, respectively, with respect to axis a—a. Therefore, a translation of Δx will result in a translation of Δy given by $$\frac{\Delta x}{\Delta y} = \cot 30^\circ = \tan 60^\circ \tag{2}$$

$$\Delta x = \Delta y \cdot \tan 60^\circ \tag{3}$$

and using equation (1) and (3), the number of steps in the x direction for a given displacement in the y-direction is given in inches by $$\Delta x_{steps} = \Delta y \cdot \tan 60^\circ (19200) \tag{4}$$

Figure 7:
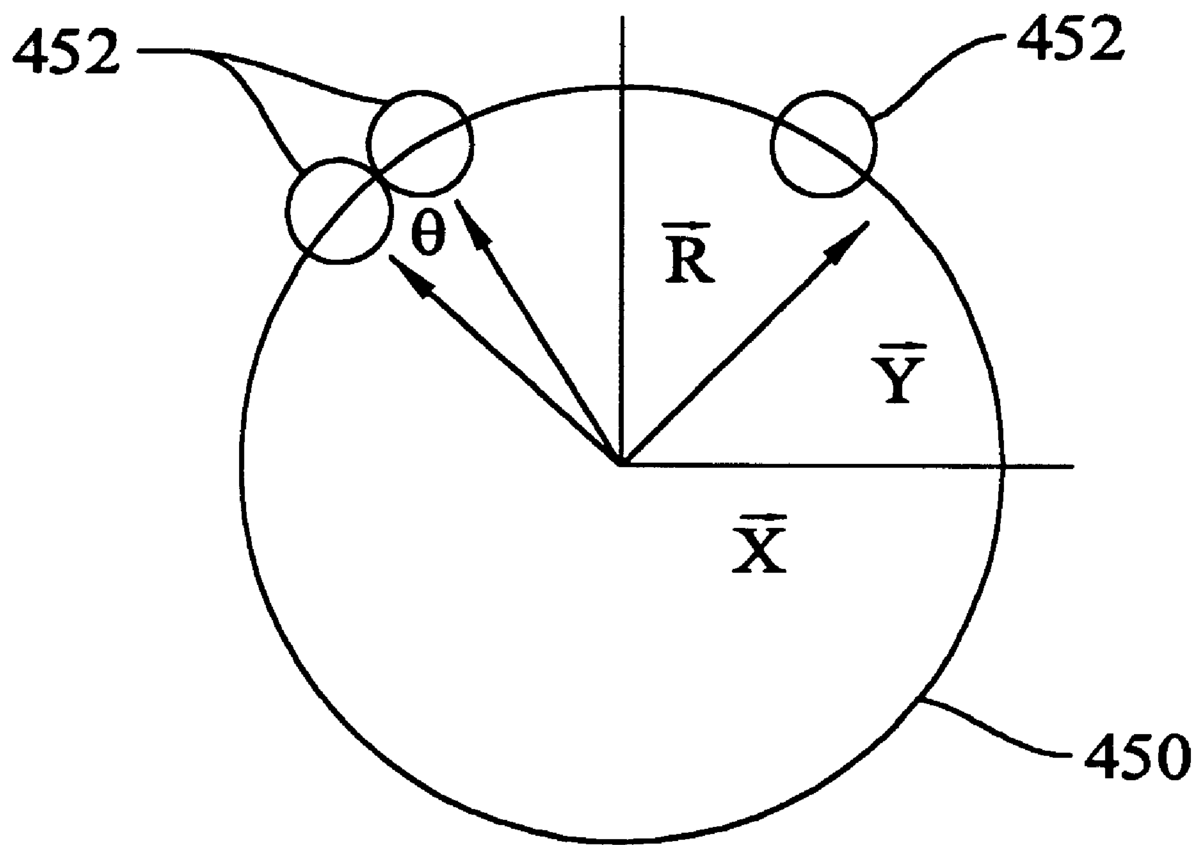
FIG. 7 illustrates illumination spots from the optical signal arranged in a circular pattern on the sapphire window.

Combinations of Δx and Δy displacements may be achieved using translation system 300 to move cam follower 328 and hence, optical system 332 mounted to cam follower 328, in a circular pattern. Shown in FIG. 7 is a circle 450, representing the area of window 362 (FIG. 5), having radius R and a beam spot 452, representing the area illuminated on window 362 by optical signal 382, having radius r. The number of spots 452 which fit on circle 450 without overlap is determined by $$\text{Number of Spots} = \frac{2\pi R}{2r} \tag{5}$$

Therefore, the angle, θ, between each adjacent spot 452 is given by $$\text{Angle between spots, } \theta = \frac{360^\circ}{\text{Number of Spots}} \tag{6}$$

The Host 52 Basic software operating in microprocessor 424 prompts a human to input the desired circle radius R and radius r of the beam spot 452 to computer 422 as input signal 423. Radius R of circle 450 is given by $$\vec{R} = \vec{X} + \vec{Y} \tag{7}$$

Where $$|\vec{X}| = |\vec{R}| \cos\theta \rightarrow x_{steps} = |\vec{R}| \cos\theta (19200)\text{ Inches} \tag{8}$$

And $$|\vec{Y}| = |\vec{R}| \sin\theta \rightarrow y_{steps} = |\vec{R}| \sin\theta \cdot \tan 60^\circ (19200)\text{ Inches} \tag{9}$$

In order to transform between polar coordinates and the required stepper motor inputs two unit vectors are defined whose magnitude is a single CCW step of a given motor 400:

$$\hat{u}_{ccw} = +\hat{u}\text{ is a single CCW step of the UP motor} \tag{10}$$

And $$\hat{d}_{ccw} = +\hat{d}\text{ is a single CCW step of the DOWN motor} \tag{11}$$

Combining the two unit vectors to transform between the polar coordinate reference frame and the motor rotation reference may be achieved by considering the relation between the rotation of a motor drive system 304 and/or 316 the corresponding translation of cams 308 and 320. Translation in the +X direction requires both motor drive systems 304 and 316 to rotate CW. Translation in the −X direction requires both motor drive systems 304 and 316 to rotate CCW. Motion in the +Y direction requires the motor drive system 304 to rotate CCW and motor drive system 316 to rotate CW. Motion in the −Y direction requires motor drive system 304 to rotate CW and motor drive system 316 to rotate CCW. In order to maintain proper contact between cam follower 328, and cams 308 and 320, for both +X and −X translations of cam follower, 328, cams 308 and 320 are generally translated equal distances in the same direction.

Thus, the vectors, $\vec{X}$, $\vec{Y}$, and $\vec{R}$ can be written in terms of motor steps as:

$$+\vec{X}=|\vec{R}|\cos\theta(19200)(\hat{u}+\hat{d}) \quad (12)$$

$$+\vec{Y}=|\vec{R}|\sin\theta(19200)\tan 60°(\hat{u}-\hat{d}) \quad (13)$$

$$\vec{R}=\vec{X}+\vec{Y}=19200|\vec{R}|(\cos\theta+\sin\theta\tan 60°)\hat{u}+192000|\vec{R}|(\cos\theta-\sin\theta\tan 60°)\hat{d} \quad (14)$$

For a combination of input steps given by the coefficients of the rotation unit vectors (where CCW is + and CW is −) cam follower 328 moves in polar coordinates according to equation 14.

Software implemented by microcomputer 424, such as Host 52 BASIC, uses the values determined by equations (5) and (6) to compute the number of steps for the motor drive systems 304 and 316 by equations (8) and (9) to provide circular motion for cam follower 328 and optical system 332 in accordance with equation (14).

In a typical operation of translation system 300, cams 308 and 320 are started from the stops (max CCW displacement for motor drive system 316 and max CW for motor drive system 304) and then translated so that the optical signal 382 is centered in window 362. However, at this stage, optical signal 382 is not being emitted. Such positioning of cam follower 328 results from 6811 steps CW for motor drive system 304 and 6811 steps CCW for motor drive system 316. This "centers" optical system 332 with respect to window 362, where by way of example, window 362 has a useful area having a 0.375 inch diameter. While optical signal 382 is being generated, cam follower 328, and hence optical system 332, are positioned so that optical signal 382 is directed to the desired radius and angle on window 362 by the motor drive systems 304 and 316 according to equation (14). Optical signal 382 is moved from point to point on a given radius circle on window 362 as microcomputer 424 recalculates equation (14) for the various angles specified in equation (6) taking the difference in steps between the current position of cam follower 328 and its recalculated position. The software implemented in microcontroller 424 also steps the radius from the center of circle 450 (representing the center of window 362) at which the center of optical signal 382 irradiates window 362, i.e., the center of irradiation. Such stepping of the center of irradiation may be about one diameter of optical signal 382 after the completion of a circle to form a pattern of concentric circles with preferably no overlap. However, the scope of the invention includes directing translation system 300 so that optical signal 382 may irradiate window 362 in other suitable patterns as well.

If translation system 300 is going to be shutdown and later used again, the Host 52 BASIC software operating in microcomputer 424 has the capability to save all existing radii and angle parameters. Saving such parameters has the benefit of facilitating continuing use of system 300 so that optical system 332 is positioned whereby optical signal 382 illuminates window 362 at the immediately preceding spot of illumination. The benefit of this feature is that it allows optimum use of sapphire window 362 before the window needs to be replaced.

Obviously, many modifications and variations of the present invention are possible in light of the above teachings. It is therefore to be understood that within the scope of the appended claims, the invention may be practiced otherwise than as specifically described.

APPENDIX 1

```
10 MTOP=3FFFH: GOSUB 1920
20 HZ=200:HZ = (461250/HZ):OPT1=0:OPT2=0:OPT3=0
30 IRAD=0:RAD=0:FD=0:FU=0:SS=3
40 INC=0:CHO=0:SP=0:AG=(PI/3)
50 DIRECT1=0:DIRECT2=0:PTL1=0:PTL2=0:MOT=0:BLOCK1=0:BLOCK2=0
60 PRINT "For motor direction and steps press:"
70 print "at 51 Rad=",rad:print "Irad=",irad:print "Deltarad=",deltarad
80 PRINT "1 for DOWN motor"
90 PRINT "2 for UP motor"
100 PRINT "3 for both motors"
110 PRINT "4 to start circle"
120 PRINT "5 to retrieve circle position and continue"
130 PRINT "6 to goto center from lock-out"
140 INPUT "7 to end program",MOT
150 IF MOT<1 THEN GOTO 60
160 IF MOT>7 THEN GOTO 60
170 IF MOT=1 THEN GOSUB 250
180 IF MOT=2 THEN GOSUB 290
190 IF MOT=3 THEN GOSUB 530
200 IF MOT=4 THEN GOTO 1040
210 IF MOT=5 THEN GOSUB 2100 : GOTO 1530
220 IF MOT=6 THEN GOSUB 1820 : GOTO 60
230 IF MOT=7 THEN END
240 GOTO 60
250 PRINT:PRINT:PRINT:PRINT:PRINT:PRINT
260 INPUT "Enter amount of steps for DOWN motor",PTL1
270 IF PTL1<1 THEN GOTO 260
280 INPUT "Press 1 for IN or 2 for OUT for DOWN motor",DIRECT1
290 IF DIRECT1<1 THEN GOTO 280
300 IF DIRECT1>2 THEN GOTO 280
310 IF DRIECT1=1 THEN PORT1=PORT1.OR.080H
320 IF DIRECT1=2 THEN PORT1=PORT1.AND.04FH
330 BLOCK1=0
```

APPENDIX 1-continued

```
340 BLOCK1=BLOCK1+SS
350 IF BLOCK1>PTL1 THEN GOTO 800
360 PUSH HZ,HZ,SS
370 CALL 0F060H
380 GOTO 340
390 PRINT:PRINT:PRINT:PRINT:PRINT:PRINT
400 INPUT"Enter amount of steps for UP motor",PTL2
410 IF PTL2<1 THEN GOTO 400
420 INPUT "Press 1 for IN or 2 for OUT for UP motor",DIRECT2
430 IF DIRECT2<1 THEN GOTO 420
440 IF DIRECT2>2 THEN GOTO 420
450 IF DIRECT2=1 THEN PORT1=PORT1.AND.0BFH
460 IF DIRECT2=2 THEN PORT1=PORT1.OR.040H
470 BLOCK2=0
480 BLOCK2=BLOCK2+SS
490 IF BLOCK2>PTL2 THEN GOTO 880
500 PUSH HZ,HZ,SS
510 CALL 0F064H
520 GOTO 480
530 PRINT:PRINT:PRINT:PRINT:PRINT:PRINT
540 INPUT "Enter amount of steps for DOWN motor",PTL1
550 IF PTL1<1 THEN GOTO 540
560 INPUT "Enter amount of steps for UP motor",PTL2
570 IF PTL2<1 THEN GOTO 560
580 INPUT "Press 1 for IN or 2 for OUT for DOWN motor",DIRECT1
590 IF DIRECT1<1 THEN GOTO 580
600 IF DIRECT1>2 THEN GOTO 580
610 IF DIRECT1=1 THEN PORT1=PORT1.OR.080H
620 IF DIRECT1=2 THEN PORT1=PORT1.AND.04FH
630 INPUT "Press 1 for IN or 2 for OUT for UP motor",DIRECT2
640 IF DIRECT2<1 THEN GOTO 630
650 IF DIRECT2>2 THEN GOTO 630
660 IF DIRECT2=1 THEN PORT1=PORT1.AND.0BFH
670 IF DIRECT2=2 THEN PORT1=PORT1.OR.040H
680 BLOCK1=0:BLOCK2=0
690 IF BLOCK1>PTL1.AND.BLOCK2>PTL2 THEN GOTO 960
700 BLOCK1=BLOCK1+SS
710 IF BLOCK1>PTL1 THEN GOTO 740
720 PUSH HZ,HZ,SS
730 CALL 0F060H
740 BLOCK2=BLOCK2+SS
750 IF BLOCK2>PTL2.AND.BLOCK1>PTL1 THEN GOTO 960
760 IF BLOCK2>PTL2 THEN GOTO 690
770 PUSH HZ,HZ,SS
780 CALL 0F064H
790 GOTO 690
800 PRINT:PRINT:PRINT:PRINT:PRINT:PRINT"]Press:"
810 PRINT "1 to repeat or"
820 PINRT "2 to return to main menu",OPT1
830 PRINT:PRINT:PRINT:PRINT:PRINT:PRINT
840 IF OPT1<1 THEN GOTO 800
850 IF OPT1>2 THEN GOTO 800
860 IF OPT1=1 THEN GOTO 330
870 IF OPT1=2 THEN RETURN
880 PRINT:PRINT:PRINT:PRINT:PRINT:PRINT" Press:"
890 PRINT "1 to repeat or"
900 INPUT "2 to return to main menu ",OPT2
910 PRINT:PRINT:PRINT:PRINT:PRINT:PRINT
920 IF OPT2<1 THEN GOTO 880
930 IF OPT2>2 THEN GOTO 880
940 IF OPT2=1 THEN GOTO 470
950 IF OPT2=2 THEN RETURN
960 PRINT:PRINT:PRINT:PRINT:PRINT:PRINT"Press:"
970 PRINT " 1 to repeat or"
980 INPUT " 2 to return to main menu ",OPT3
990 PRINT:PRINT:PRINT:PRINT:PRINT:PRINT
1000 IF OPT3<1 THEN GOTO 960
1010 IF OPT3>2 THEN GOTO 960
1020 IF OPT3=1 THEN GOTO 680
1030 IF OPT3=2 THEN RETURN
1040 PRINT:PRINT:PRINT:PRINT:PRINT:PRINT
1050 INPUT "Enter value for SPOT SIZE in um (range= 0 to 2000um)",SP
1060 IF SP<0 THEN GOTO 1050
1070 IF SP>2000 THEN GOTO 1050
1080 SP=SP*.0001/2.54
1090 PRINT:PRINT:PRINT:PRINT:PRINT:PRINT
1100 INPUT "Enter value for R in inches (range= 0 to .17)",RAD
1110 IF RAD<0 THEN 1100
1120 IF RAD>.17 THEN 1100
```

APPENDIX 1-continued

```
1130 INC=0:FA=0:FB=0:AN=(SP/RAD);AN1=AN
1140 DELTARAD=RAD-IRAD
1150 print "at 1072 Rad=",rad:print "Irad=",irad:print "Deltarad=",deltarad
1160 PRINT "THE NUMBER OF STEPS IN THIS CIRCLE IS ",2*PI/AN1
1170 V0=PORT1.AND.1
1180 IF V0=1 THEN PRINT : PRINT "Turn the blue box off"
1190 FOR DELAY=1 TO 1000:NEXT DELAY
1200 V0=PORT1.AND.1
1210 IF V0=1 THEN GOTO 1180
1220 DELTAFD=19200*DELTARAD*(COS(0)-TAN(AG)*SIN(0))
1230 DELTAFU=19200*DELTARAD*(COS(0)+TAN(AG)*SIN(0))
1240 ID=FD+DELTAFD:IU=FU+DELTAFU
1250 DELTAFD=ABS(DELTAFD):DELTAFU=ABS(DELTAFU)
1260 BLOCK1=0:BLOCK2=0
1270 PORT1=PORT1.AND.04FH:REM Down motor out
1280 PORT1=PORT1.AND.0BFH:REM Up motor in
1290 BLOCK1=BLOCK1+SS
1300 PUSH HZ,HZ,SS
1310 CALL 0F060H
1320 BLOCK2=BLOCK2+SS
1330 PUSH HZ,HZ,SS
1340 CALL 0F064H
1350 IF BLOCK1>=DELTAFD.AND.BLOCK2>=DELTAFU THEN GOTO 1370
1360 GOTO 1290
1370 V0=PORT1.AND.1
1380 IF V0=0 THEN PRINT : PRINT "Turn blue box on"
1390 FOR DELAY=1 to 1000:NEXT DELAY
1400 V0=PORT1.AND.1
1410 IF V0=0 THEN GOTO 1380
1420 IF V0=1 THEN GOTO 1430
1430 FD=0:FU=0:BLOCK1=0:BLOCK2=0:IRAD=RAD
1440 FD=19200*RAD*(COS(AN)-TAN(AG)*SIN(AN))
1450 FU=19200*RAD*(+TAN(AG)*SIN(AN)+COS(AN))
1460 DELTAD=FD-ID:DELTAU=FU-IU
1470 ID=FD:IU=FU
1480 IF DELTAD<0 THEN PORT1=PORT1.AND.04FH
1490 IF DELTAD<0 THEN PORT1=PORT1.OR.080H
1500 IF DELTAU>0 THEN PORT1=PORT.AND.0BFH
1510 IF DELTAU<0 THEN PORT1=PORT1.OR.040H
1520 BLK1=ABS(DELTAD):BLK2=ABS(DELTAU)
1530 V0=PORT1.AND.1
1540 IF V0=1 THEN GOSUB 1760
1550 CC=GET : IF CC=ASC(S) THEN GOTO 2010
1560 IF BLOCK1>=BLK1 THEN GOTO 1600
1570 BLOCK1=BLOCK1+1
1580 PUSH HZ,HZ,1
1590 CALL 0F060H
1600 IF BLOCK2>=BLK2 THEN GOTO 1640
1610 BLOCK2=BLOCK2+1
1620 PUSH HZ,HZ,1
1630 CALL 0F064H
1640 IF BLOCK1>=BLK1.AND.BLOCK2>=BLK2 THEN GOTO 1660
1650 GOTO 1530
1660 IF AN=2*PI THEN GOTO 1710
1670 IF RAD<=0 THEN PRINT "Finished!!!" : STOP
1680 AN=AN+AN1:BLK1=0:BLK2=0
1690 IF AN<2*PI THEN GOTO 1430 ELSE AN=2*PI
1700 GOTO 1430
1710 RAD=RAD-SP
1720 AN=(SP/RAD):AN1=AN
1730 print "at 1690 Rad=",rad
1740 PRINT "THE NUMBER OF STEPS IN THIS CIRCLE IS",2*PI/AN1
1750 GOTO 1430
1760 PRINT:PRINT "Motors stopped"
1770 CC=GET : IF CC=ASC(S) THEN GOTO 2020
1780 V0=PORT1.AND.1
1790 IF V0=0 THEN PRINT:PRINT "Motors moving"
1800 IF V0=0 THEN RETURN
1810 GOTO 1770
1820 PORT1=PORT1.AND.0BFH
1830 PORT1=PORT1.OR.080H
1840 BLOCK1=0
1850 BLOCK1=BLOCK1+SS
1860 PUSH HZ,HZ,SS
1870 CALL 0F060H
1880 PUSH HZ,HZ,SS
1890 CALL 0F064H
1900 IF BLOCK1>6811 THEN RETURN
1910 GOTO 1850
```

APPENDIX 1-continued

```
1920 A=7000H : CS=18495
1930 READ D
1940 IF (D=0A5H.AND.K=0A4H) THEN GOTO 1990
1950 XBY(A)=D
1960 C=C+D:K=D
1970 A=A+1
1980 GOTO 1930
1990 IF (C<>CS) THEN PRINT "DATA ERROR IN SAVE CFG-",CS,C : STOP
2000 RETURN
2010 GOSUB 2310
2020 P=0
2030 PUSH P
2040 CALL 7000H
2050 POP S
2060 PRINT
2070 IF (S=0) THEN PRINT "Storage OK" ELSE PRINT "Storage ERROR" : END
2080 GOSUB 2100
2090 END
2100 P=0
2110 FOR X=0 TO 63
2120 XBY(7FC0H+X)=XBY(0F800H+(P*64)+X)
2130 NEXT X
2140 LD@ 7FC5H:POP SP:?"SP=",SP,
2150 LD@ 7FCBH:POP RAD:?"RAD=",RAD,
2160 LD@ 7FD1H:POP BLOCK1:?"BLOCK1=",BLOCK1,
2170 LD@ 7FD7H:POP BLOCK2:?"BLOCK2=",BLOCK2,
2180 LD@ 7FDDH:POP AN:?"AN=",AN
2190 LD@ 7FE3H:POP BLK1:?"BLK1=",BLK1,
2200 LD@ 7FE9H:POP BLK2:?"BLK2=",BLK2,
2210 LD@ 7FEFH:POP ID:?"ID=",ID,
2220 LD@ 7FF5H:POP IU:?"IU=",IU,
2230 LD@ 7FFBH:POP A:?A
2240 AN1=(SP/RAD)
2250 V0=PORT1.AND.1
2260 IF V0=0 THEN PRINT : PRINT "Turn blue box on"
2270 FOR DELAY=1 TO 1000: NEXT DELAY
2280 IF V0=0 THEN GOTO 2250
2290 RETURN
2300 REM Store in RAM Buffer
2310 PUSH SP:ST@ 7FC5H
2320 PUSH RAD:ST@ 7FCBH
2330 PUSH BLOCK1:ST@ 7FD1H
2340 PUSH BLOCK2:ST@ 7FD7H
2350 PUSH AN:ST@ 7FDDH
2360 PUSH BLK1:ST@ 7FE3H
2370 PUSH BLK2:ST@ 7FE9H
2380 PUSH ID:ST@ 7FEFH
2390 PUSH IU:ST@ 7FF5H
2400 PUSH A:ST@ 7FFBH
2410 RETURN
2420 DATA 0C0H, 0A8H
2430 DATA 0C2H, 0AFH
2440 DATA 074H, 001H
2450 DATA 012H, 000H, 030H
2460 DATA 0C3H
2470 DATA 0E9H
2480 DATA 094H, 00AH
2490 DATA 040H, 002H
2500 DATA 079H, 009H
2510 DATA 090H, 0D5H, 055H
2520 DATA 074H, 0AAH
2530 DATA 0F0H
2540 DATA 090H, 0AAH, 0AAH
2550 DATA 074H, 055H
2560 DATA 0F0H
2570 DATA 090H, 0D5H, 055H
2580 DATA 074H, 0A0H
2590 DATA 0F0H
2600 DATA 074H, 040H
2610 DATA 089H, 0F0H
2620 DATA 0A4H
2630 DATA 090H, 07FH, 0C0H
2640 DATA 07AH, 000H
2650 DATA 07BH, 0F8H
2660 DATA 0C3H
2670 DATA 02AH
2680 DATA 0FAH
2690 DATA 0E5H, 0F0H
2700 DATA 03BH
```

APPENDIX 1-continued

```
2710 DATA 0FBH
2720 DATA 075H, 0F0H, 03FH
2730 DATA 012H, 070H, 067H
2740 DATA 07FH, 064H
2750 DATA 0DFH, 0FEH
2760 DATA 07EH, 000H
2770 DATA 07FH, 064H
2780 DATA 0E0H
2790 DATA 0B5H, 0F0H, 002H
2800 DATA 080H, 008H
2810 DATA 0DEH, 0F8H
2820 DATA 0DFH, 0F6H
2830 DATA 078H, 0FFH
2840 DATA 080H, 002H
2850 DATA 078H, 000H
2860 DATA 090H, 000H, 000H
2870 DATA 0D5H, 082H, 0FDH
2880 DATA 0D5H, 083H, 0FAH
2890 DATA 0D0H, 0A8H
2900 DATA 07AH, 000H
2910 DATA 074H, 09AH
2920 DATA 012H, 000H, 030H
2930 DATA 022H
2940 DATA 0E0H
2950 DATA 0C0H, 082H
2960 DATA 0C0H, 083H
2970 DATA 08AH, 082H
2980 DATA 08BH, 083H
2990 DATA 0F0H
3000 DATA 0A3H
3010 DATA 0AAH, 082H
3020 DATA 0ABH, 083H
3030 DATA 0D0H, 083H
3040 DATA 0D0H, 082H
3050 DATA 0D5H, 0F0H, 003H
3060 DATA 0F5H, 0F0H
3070 DATA 022H
3080 DATA 0A3H
3090 DATA 080H, 0E4H
3100 DATA 0A5H, 0A5H
```

We claim:

1. A translation system for directing an optical signal to predetermined coordinates, comprising:

a tube having a sidewall and an aperture through said sidewall;

an optical system for emitting an optical signal through said aperture; and a mechanism mounted within said tube for moving said optical system along a two dimensional path to direct said optical signal through selected coordinates of said aperture.

2. The system of claim 1 wherein said mechanism moves said optical system only when said optical system emits said optical signal.

3. The system of claim 1 wherein said translation mechanism moves said optical system so that said optical signal is transmitted through selected regions of said window in a predetermined pattern.

4. A system for directing an optical signal to predetermined coordinates, comprising:

a tube having a sidewall and an aperture through said sidewall;

an optical system for emitting an optical signal through said aperture; and a mechanism mounted within said tube for moving said optical system along a two dimensional path to direct said optical signal through selected coordinates of said aperture, where said mechanism includes:

a frame mounted in said tube;

a first motor drive system;

a first cam which slides in said frame upon actuation of said first motor drive system a second motor drive system:

a second cam which slides in said frame upon actuation of said second motor drive system; and a cam follower in contact with said first and second cams which translates when said first and second cams slide in said frame, and which supports said optical system.

5. The system of claim 4 further including a controller for directing said translation mechanism so that said cam follower translates said optical system along two orthogonal vectors.

6. The system of claim 5 wherein the position of said optical system is constant with respect to said window when said controller receives a logic input signal having a predetermined logic level.

7. The system of claim 4, further including a controller for controlling the directions and angular displacements of said first and second motor drive systems.

8. The system of claim 4 further including a spring interposed between said cam follower and said frame for urging said cam follower against said first and second cams.

9. The system of claim 4 wherein:

said first cam has a generally planar first cam surface having a first normal that is non-parallel with respect to the direction of travel of said first cam;

said second cam has a generally planar cam surface having a second normal that is non-parallel with respect to the direction of travel of said second cam; and said cam follower has a third generally planar surface in contact with said first cam surface, and a fourth generally planar surface in contact with said second cam surface, where said third and fourth planar surfaces are non-parallel.

10. The system of claim 4 wherein:

said first motor drive system includes:

a first stepping motor;

a first gear reducer operably coupled to said first stepping motor for providing a first angular output signal having a first angular displacement and a first angular direction;

a first screw drive coupled between said first gear reducer and said first cam which causes said first cam to slide in said frame when said screw drive receives said first angular output signal; and said second motor drive system includes:

a second stepping motor;

a second gear reducer operably coupled to said second stepping motor for providing a second angular output signal having a second angular displacement and a second angular direction; and a second screw drive coupled between said second gear reducer and said second cam which causes said second cam to slide in said frame when said screw drive receives said second angular output signal.

11. A translation system for directing an optical signal to predetermined coordinates, comprising:

a tube having a sidewall and an aperture through said sidewall;

an optical system for emitting an optical signal through said aperture;

a mechanism mounted within said tube for moving said optical system along a two dimensional path to direct said optical signal through selected coordinates of said aperture; and a controller for enabling said mechanism when said controller receives a logic signal representing emission of said optical signal.

12. A system for directing an optical signal to predetermined coordinates, comprising:

an optical system for emitting an optical signal; and a mechanism for moving said optical system along a two dimensional path to direct said optical signal to selected coordinates, where said mechanism includes:

a frame;

a first motor drive system;

a first cam which translates in said frame upon actuation of said first motor drive system a second motor drive system:

a second cam which translates in said frame upon actuation of said second motor drive system; and a cam follower in contact with said first and second cams which translates when said first and second cams translate in said frame, and which supports said optical system.

* * * * *